(12) United States Patent
Ku et al.

(10) Patent No.: US 8,139,233 B2
(45) Date of Patent: Mar. 20, 2012

(54) SYSTEM AND METHOD FOR VIA STRUCTURE MEASUREMENT

(75) Inventors: Yi Sha Ku, Hsinchu (TW); Wei Te Hsu, Banqiao (TW); Hsiu Lan Pang, Baoshan Township, Hsinchu County (TW); Deh Ming Shyu, Jhunan Township, Miaoli County (TW)

(73) Assignee: Industrial Technology Research Institute, Chutung, Hsinchu (TW)

( * ) Notice: Subject to any disclaimer, the term of this patent is extended or adjusted under 35 U.S.C. 154(b) by 245 days.

(21) Appl. No.: 12/725,930

(22) Filed: Mar. 17, 2010

(65) Prior Publication Data

US 2011/0172974 A1 Jul. 14, 2011

(30) Foreign Application Priority Data

Jan. 8, 2010 (TW) .............................. 99100341 A (51) Int. Cl.
*G01B 11/00* (2006.01)
(52) U.S. Cl. ..................................... 356/626; 356/241.1
(58) Field of Classification Search ................... 356/626, 356/241.1; 250/559.19, 559.22
See application file for complete search history.

(56) References Cited

U.S. PATENT DOCUMENTS

| 7,045,455 | B2 | 5/2006 | Zhang et al. |
| 7,471,384 | B2 * | 12/2008 | Nomaru et al. ............ 356/241.1 |
| 2003/0107728 | A1 | 6/2003 | Belk et al. |
| 2004/0123651 | A1 | 7/2004 | Hantschel et al. |
| 2007/0257191 | A1 | 11/2007 | Kadyshevitch et al. |

* cited by examiner

*Primary Examiner* — Roy M Punnoose
(74) *Attorney, Agent, or Firm* — Egbert Law Offices PLLC (57) ABSTRACT

A system for via structure measurement is disclosed. The system comprises a reflectometer, a simulation unit and a comparing unit. The reflectometer is configured to collect a measured diffraction spectrum of at least a via. The simulation unit is configured to provide simulated diffraction spectrums of the at least a via. The comparing unit is configured to determine at least a depth and at least a bottom profile of the at least a via by comparing the collected diffraction spectrum and the simulated diffraction spectrums.

21 Claims, 14 Drawing Sheets

SYSTEM AND METHOD FOR VIA STRUCTURE MEASUREMENT

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The disclosure relates to a system and a method for semiconductor structure measurement, and particularly, to a system and a method for via structure measurement.

2. Description of Related Art Including Information Disclosed Under 37 CFR 1.97 and 37 CFR 1.98.

As consumer demand for lighter and smaller electronic devices continues to grow, semiconductor manufacturing techniques are advancing to meet such requirements. In particular, a new technique, known as the 3D stacking technique, has been developed. The 3D stacking technique utilizes through silicon via (TSV) technique, which involves vertically stacking a plurality of chips, to reduce the overall package size. TSV technique uses a via structure to vertically connect a plurality of chips, and therefore can replace wire bonding technique to save the costs of routing and intermediate layers required by wire bonding technique.

Due to the aforementioned advantages, TSV technique is popular among small-sized electronic devices with high aspect ratio. Accordingly, measurement for the via structures formed according to TSV technique has become an issue of importance. Generally, large sized via structures, e.g. via structure with aperture greater than 10 micrometers, can be measured by optical microscope. However, for via structures with high density, e.g. via structures with via/space ratio greater than 1, via structures with high aspect ratio, e.g. via structures with aspect ratio greater than 10, or via structures with small aperture, e.g. via structures with aperture smaller than 10 micrometers, most of the current measuring methods, such as measuring methods utilizing electronic microscopes or spring probes, are slow and destructive. In other words, currently, the parameters, especially the depth and the bottom profile, of via structures with high density, high aspect ratio or small aperture cannot be measured in an optical and non-destructive way.

On the other hand, TSV technique is progressing toward high-density and high aspect-ratio applications. According to the International Technology Roadmap for Semiconductor (ITRS) published in 2008, the aperture of all TSVs in the market are estimated to be smaller than 1.4 micrometer, and the aspect ratio thereof are estimated to be greater than 10.

Accordingly, there is a need to design a system and a method for via structure measurement in which the depth and bottom profile of a via structure can be measured in a non-destructive way. This disclosure provides such system and method.

BRIEF SUMMARY OF THE INVENTION

The system and method for determining via structure parameters in accordance with the exemplary embodiments provided by this disclosure determine the depth and the bottom profile of the via structures by comparing the collected diffraction spectrums and the simulated diffraction spectrums. Therefore, the structural parameters of the via structures can be determined in a fast and non-destructive way.

One embodiment discloses a system for via structure measurement. The system comprises a reflectometer, a simulation unit and a comparing unit. The reflectometer is configured to collect a measured diffraction spectrum of at least a via structure. The simulation unit is configured to provide simulated diffraction spectrums of the at least a via structure. The comparing unit is configured to determine at least a depth and at least a bottom profile of the at least a via structure by comparing the collected measured diffraction spectrum of at least a via structure and the simulated diffraction spectrums of the at least a via structure.

Another embodiment discloses a method for determining via structure parameters according to a diffraction spectrum of at least a via structure. The method comprises the steps of: obtaining a measured diffraction spectrum of at least a via structure; carrying out a calculation based upon frequency information contained in the measured diffraction spectrum; and determining at least a depth of the at least a via structure according to the calculation results.

Another embodiment discloses a method for determining the bottom profile of at least a via structure according to the reflection spectrums of the at least a via structure. The method comprises the steps of: obtaining a measured diffraction spectrum of the at least a via structure; carrying out a calculation based upon magnitude information contained in the measured diffraction spectrum; and determining at least a bottom profile of the at least a via structure according to the calculation results.

BRIEF DESCRIPTION OF THE SEVERAL VIEWS OF THE DRAWINGS

The accompanying drawings, which are incorporated in and constitute a part of this specification, illustrate embodiments of the disclosure and, together with the description, serve to explain the principles of the invention.

DETAILED DESCRIPTION OF THE INVENTION

The following systems and methods for via structure measurement in accordance with exemplary embodiments of the disclosure measure via structures according to thin film theory. Specifically, the exemplary embodiments of the disclosure utilize a reflectometer to collect diffraction spectrums of the via structures. In addition, the exemplary embodiments of the disclosure simulate diffraction spectrums of the via structures based upon the Fresnel equation, and then determine the via structure parameters by comparing the collected diffraction spectrums and the simulated diffraction spectrums. Furthermore, the exemplary embodiments of the disclosure use an ellipsoid model to simulate the bottom profile of the via structures, generate the simulated diffraction spectrums accordingly, and then determine the bottom profile of the via structures by comparing the collected diffraction spectrums and the simulated diffraction spectrums.

Figure 1:
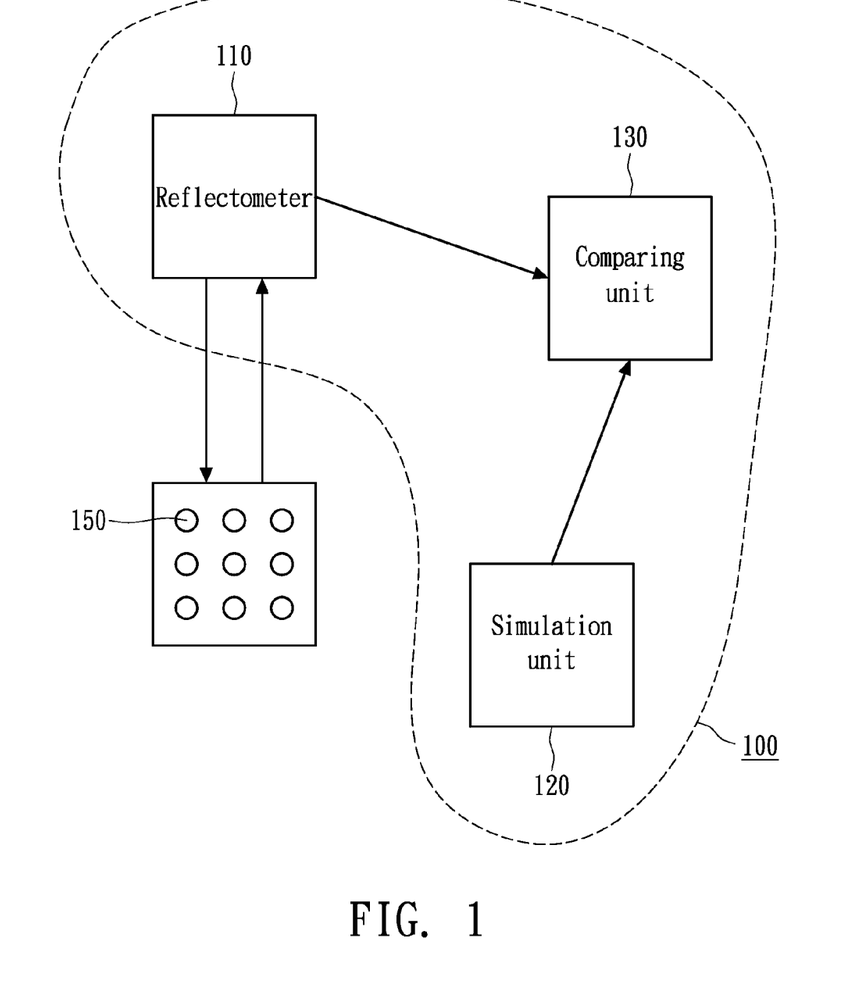
FIG. 1 illustrates the schematic view of a system for via structure measurement in accordance with an exemplary embodiment.

FIG. 1 illustrates a schematic view of a system for via structure measurement in accordance with an exemplary embodiment. As shown in FIG. 1, the system 100 comprises a reflectometer 110, a simulation unit 120 and a comparing unit 130. The reflectometer 110 is configured to collect a measured diffraction spectrum of a via structure 150. The reflectometer 110 can be any reflectometer available in the market, such as those provided by Nanometrics or Nova. The simulation unit 120 is configured to provide simulated diffraction spectrums of the via structure 150. The simulation unit 120 can be a database, comprising a plurality of simulated diffraction spectrums of via structures with different depths and different bottom profiles, or the simulation unit 120 can be a computer, which is configured to generate simulated diffraction spectrums of via structures with different depths and different bottom profiles. The comparing unit 130 is configured to determine the depth and bottom profile of the via structure 150 by comparing the collected measured diffraction provided by the reflectometer 110 and the simulated diffraction spectrums provided by the simulation unit 120. As shown in FIG. 1, the system 100 determines the structural parameters of the via structure 150 by analyzing the diffraction spectrums. Accordingly, the destruction caused by conventional measuring methods is prevented.

Figure 2:
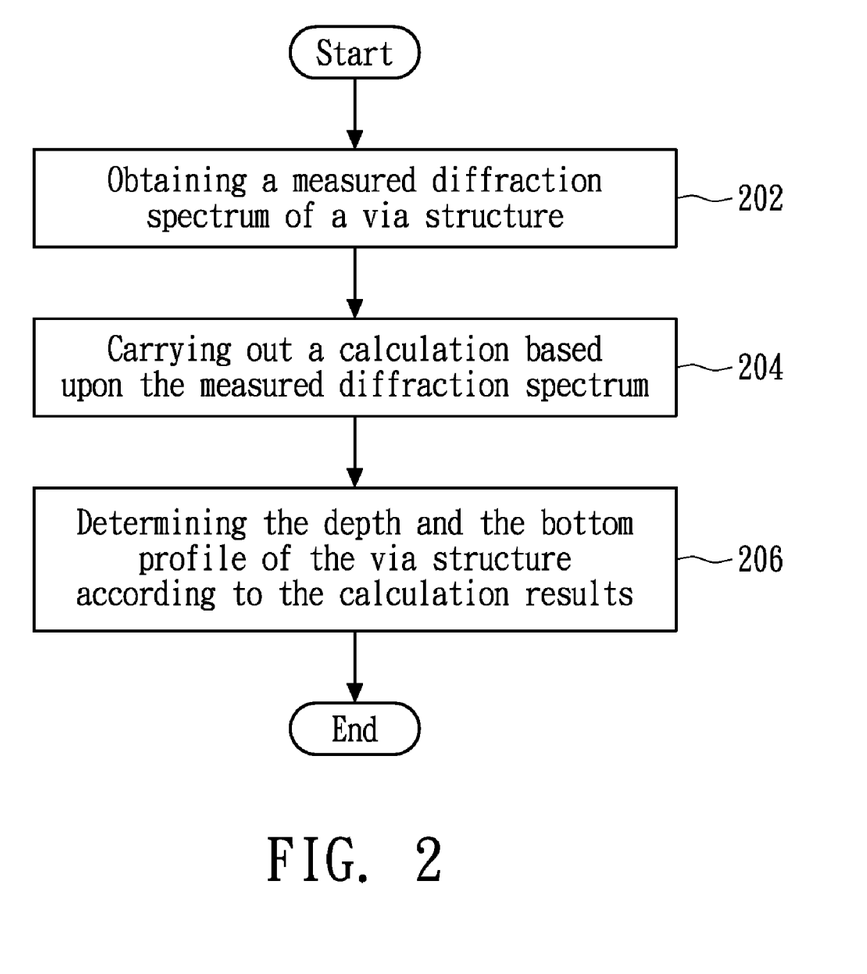
FIG. 2 is a flow chart illustrating an exemplary embodiment of the method for determining via structure parameters according to a diffraction spectrum of at least a via structure.

FIG. 2 is a flow chart illustrating an exemplary embodiment of the method for determining via structure parameters according to a diffraction spectrum of at least a via structure. In step 202, a measured diffraction spectrum of a via structure is obtained, and step 204 is executed. In step 204, a calculation is carried out based upon frequency and magnitude information contained in the measured diffraction spectrum, and step 206 is executed. In step 206, the depth of the via structure is determined according to the calculation results based upon the frequency information contained in the measured diffraction spectrum, and the bottom profile of the via structure is determined according to the calculation results based upon the magnitude information contained in the measured diffraction spectrum.

Figure 3:
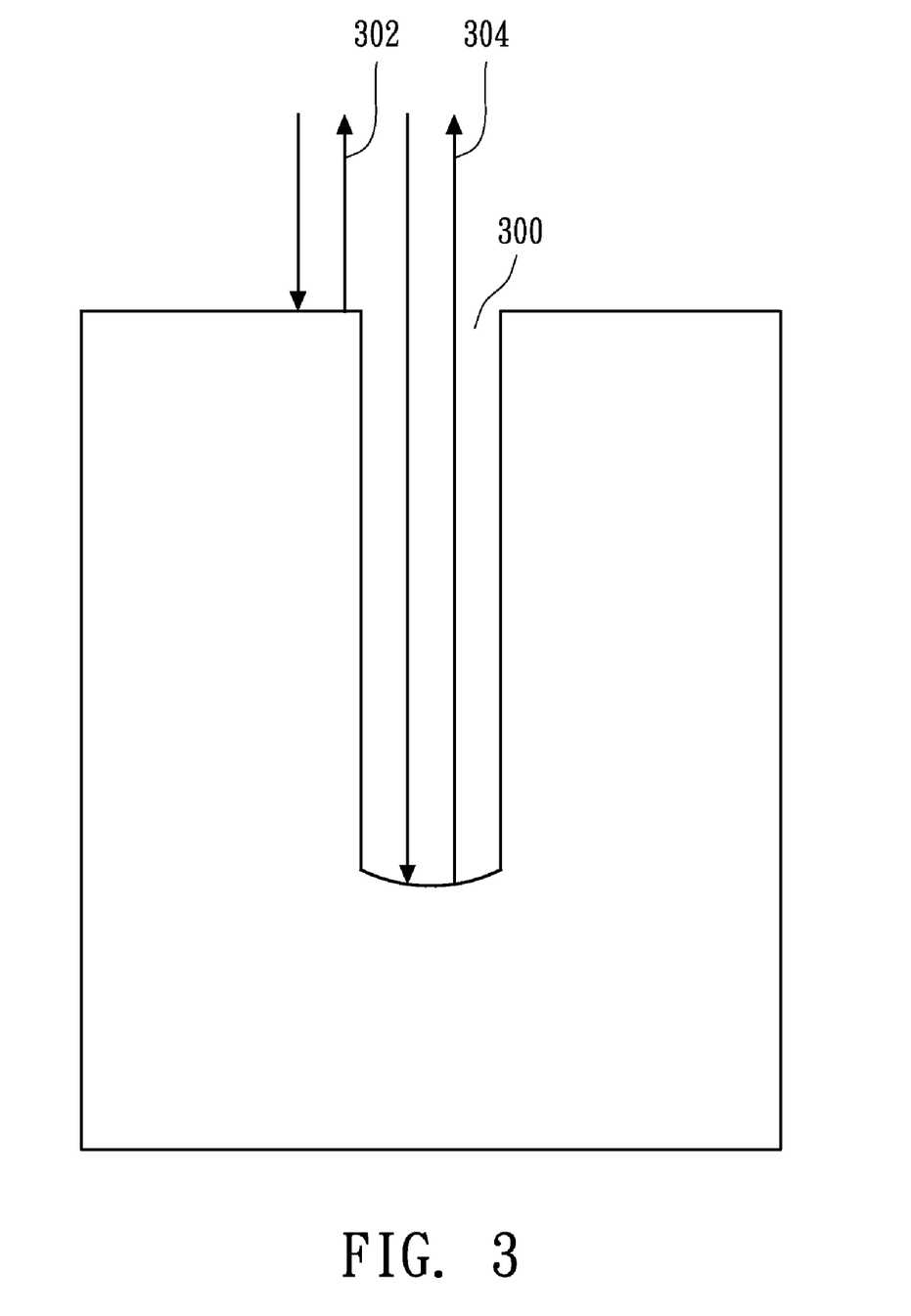
FIG. 3 shows a schematic view of a via structure with small aperture and high aspect ratio.
Figure 4:
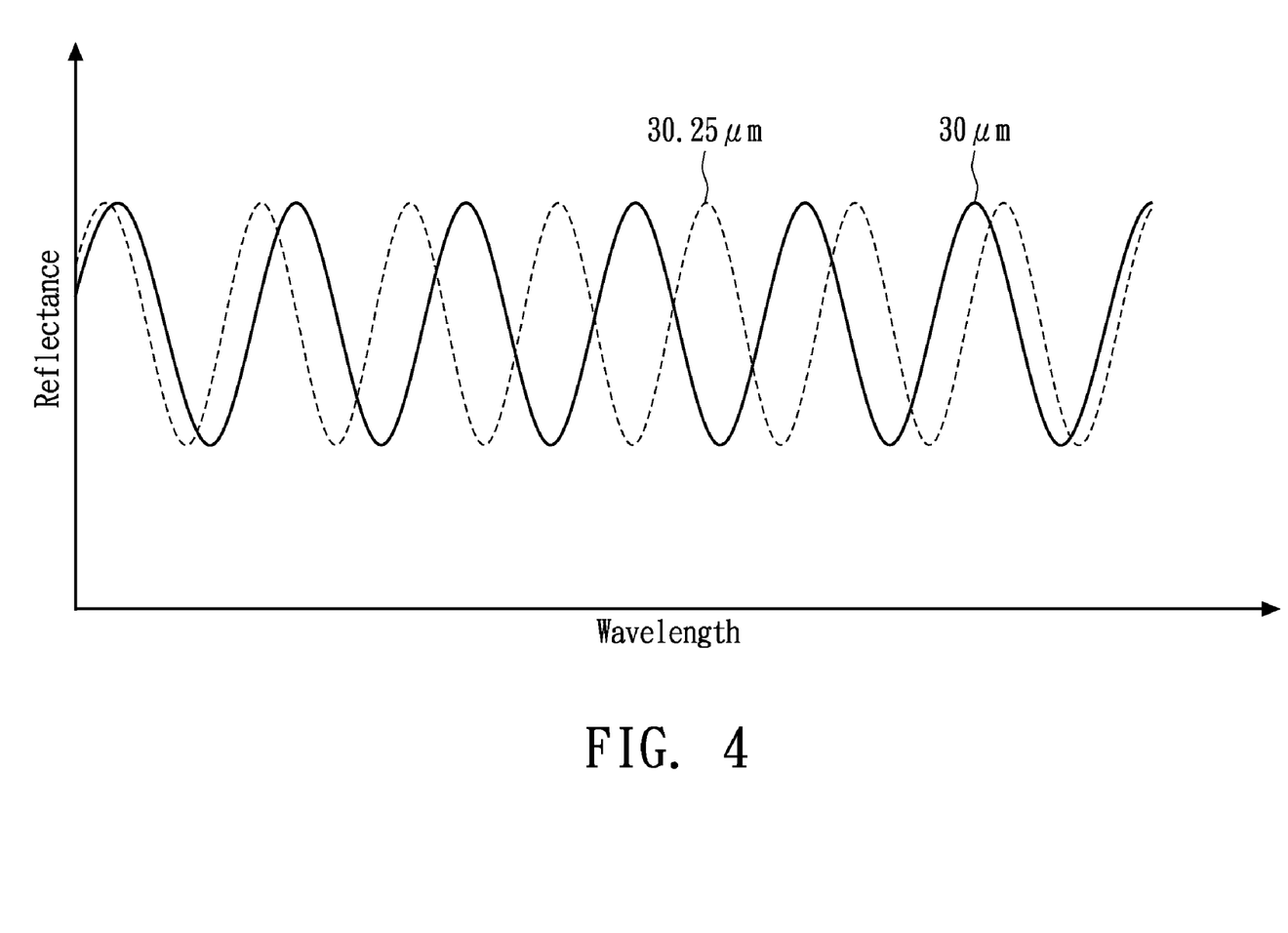
FIG. 4 shows a graphical view of the simulated diffraction spectrums for the via structures with different depths.

FIG. 3 shows a via structure 300 with small aperture and high aspect ratio. Applying the system 100 shown in FIG. 1 and the method shown in FIG. 2 to the via structure 300, the reflectometer 110 generates lights propagating perpendicularly to the via structure 300 so as to collect the diffraction spectrum of the via structure 300. As shown in FIG. 3, the reflecting lights collected by the reflectometer 110 include the light 302 reflecting from the silicon surface of the via structure 300 and the light 304 reflecting from the bottom of the via structure 300. If the phase difference of these two reflecting lights is an integer multiple of the wavelength of the generated lights, a constructive interference occurs to enhance the intensity of the reflecting lights. Accordingly to the Fresnel equation, such reflecting lights exhibit a 180 degree phase difference multiplied by a reflection value:

$$r_{si}^+ = \frac{n_0 - n}{n + n_0}$$

wherein $n_0$ represents the refractive index of air, and n represents the refractive index of silicon. Accordingly, different diffraction spectrums are generated for via structures with different depths. The simulation unit 120 simulates different diffraction spectrums for via structures with different depths according to the Fresnel equation. FIG. 4 shows the simulated diffraction spectrums for via structures with depths of 30 micrometers and 30.25 micrometers respectively. The comparing unit 130 then selects a simulated diffraction spectrum with a minimum difference compared with the measured diffraction spectrum and determines the depth of the via structure 300 according to the parameters, i.e. the depth of the selected simulated diffraction spectrum.

Figure 5:
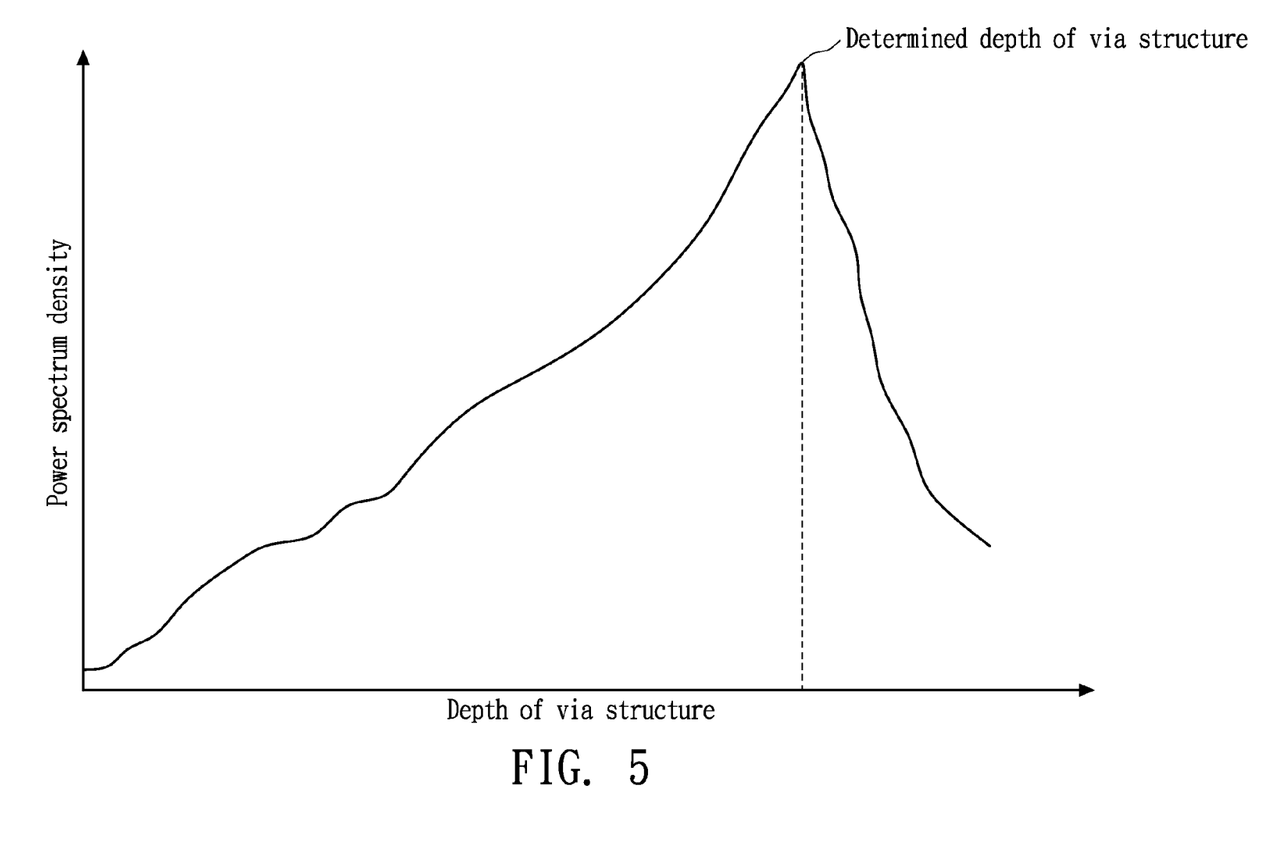
FIG. 5 shows a graphical view of the result of an inverse Fourier transform performed on a selected simulated diffraction spectrum in accordance with an exemplary embodiment.

Alternatively, in an exemplary embodiment, an inverse Fourier transform can be performed on the selected simulated diffraction spectrum to determine the depth of the via structure 300. FIG. 5 shows the result of an inverse Fourier transform performed on a selected simulated diffraction spectrum in accordance with an exemplary embodiment. The depth of the via structure can then be determined according to the result shown in FIG. 5.

Figure 6:
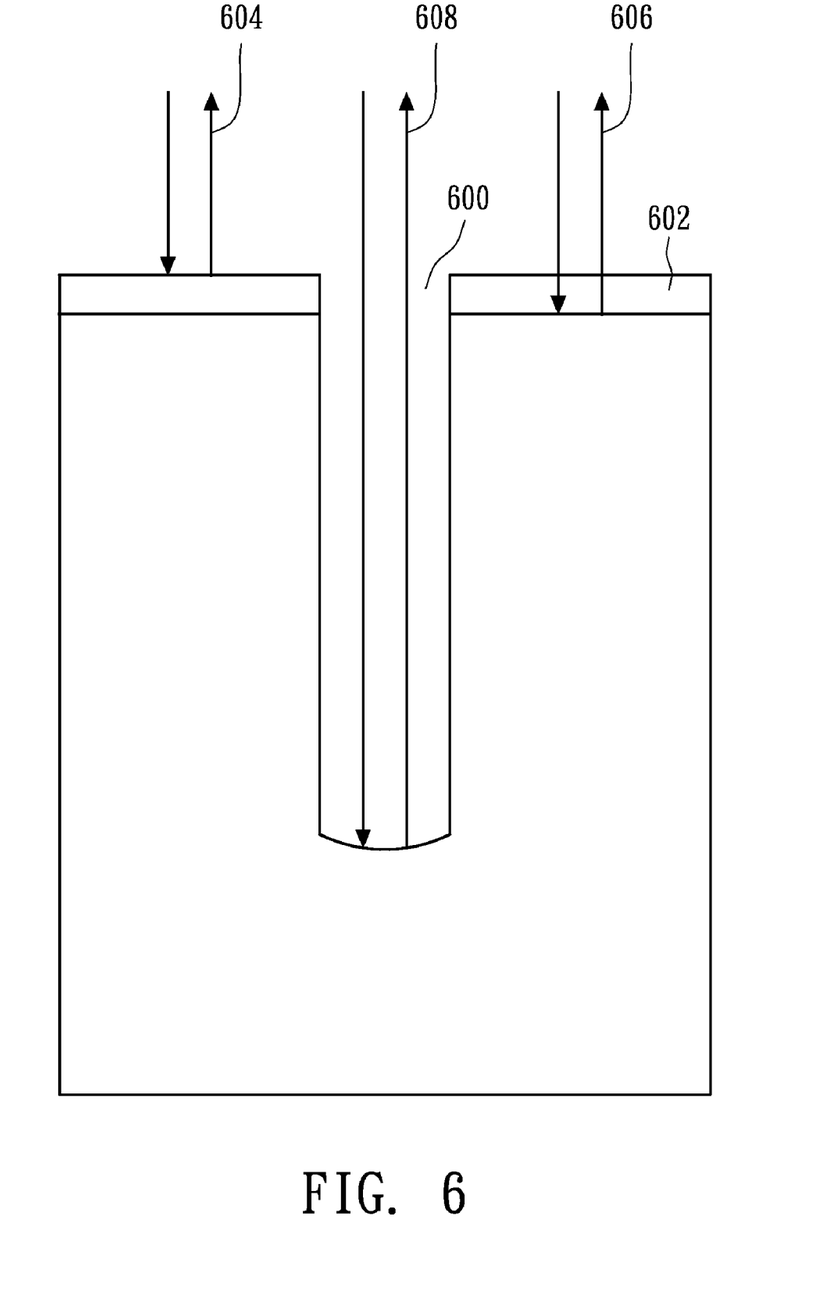
FIG. 6 shows a schematic view of another via structure with small aperture and high aspect ratio.

FIG. 6 shows another via structure 600 with small aperture and high aspect ratio. A thin film oxide layer 602 is formed on the layer of the via structure 600. Similarly, applying the system 100 shown in FIG. 1 and the method shown in FIG. 2 to the via structure 600, the reflectometer 110 generates lights propagating perpendicularly to the via structure 600 so as to collect the diffraction spectrum of the via structure 600. As shown in FIG. 6, the reflecting lights collected by the reflectometer 110 include the light 604 reflecting from the thin film oxide layer 602, the light 606 penetrating the thin film oxide layer 602 and reflecting from the silicon surface of the via structure 600, and the light 608 reflecting from the bottom of the via structure 600. If the phase difference of these reflecting lights is an integer multiple of the wavelength of the generated lights, a constructive interference occurs to enhance the intensity of the reflecting lights. Accordingly to the Fresnel equation, such reflecting lights exhibit a 180 degree phase difference. The light 604 reflecting from the thin film oxide layer 602 should be multiplied by a reflection value $$r_{ox}^+ = \frac{n_0 - n_{ox}}{n_{ox} + n_0},$$

wherein $n_0$ represents the refractive index of air, and $n_{ox}$ the refractive index of the thin film oxide layer 602. The light 606 penetrating the thin film oxide layer 602 and reflecting from the silicon surface of the via structure 600 should be multiplied by a penetrating value $$t_{ox}^- = \frac{2n_0}{n_{ox} + n_0}$$

and a reflection value.

$$r_{si}^+ = \frac{n_0 - n_{si}}{n_{si} + n_0}$$

wherein $n_{x1}$ represents the refractive index of silicon. The light 608 reflecting from the bottom of the via structure 600 should be multiplied by a reflection value $$r_{si}^+ = \frac{n_0 - n_{si}}{n_{si} + n_0}$$

Accordingly, the simulation unit 120 simulates different diffraction spectrums for via structures with different depths according to the Fresnel equation.

Figure 7:
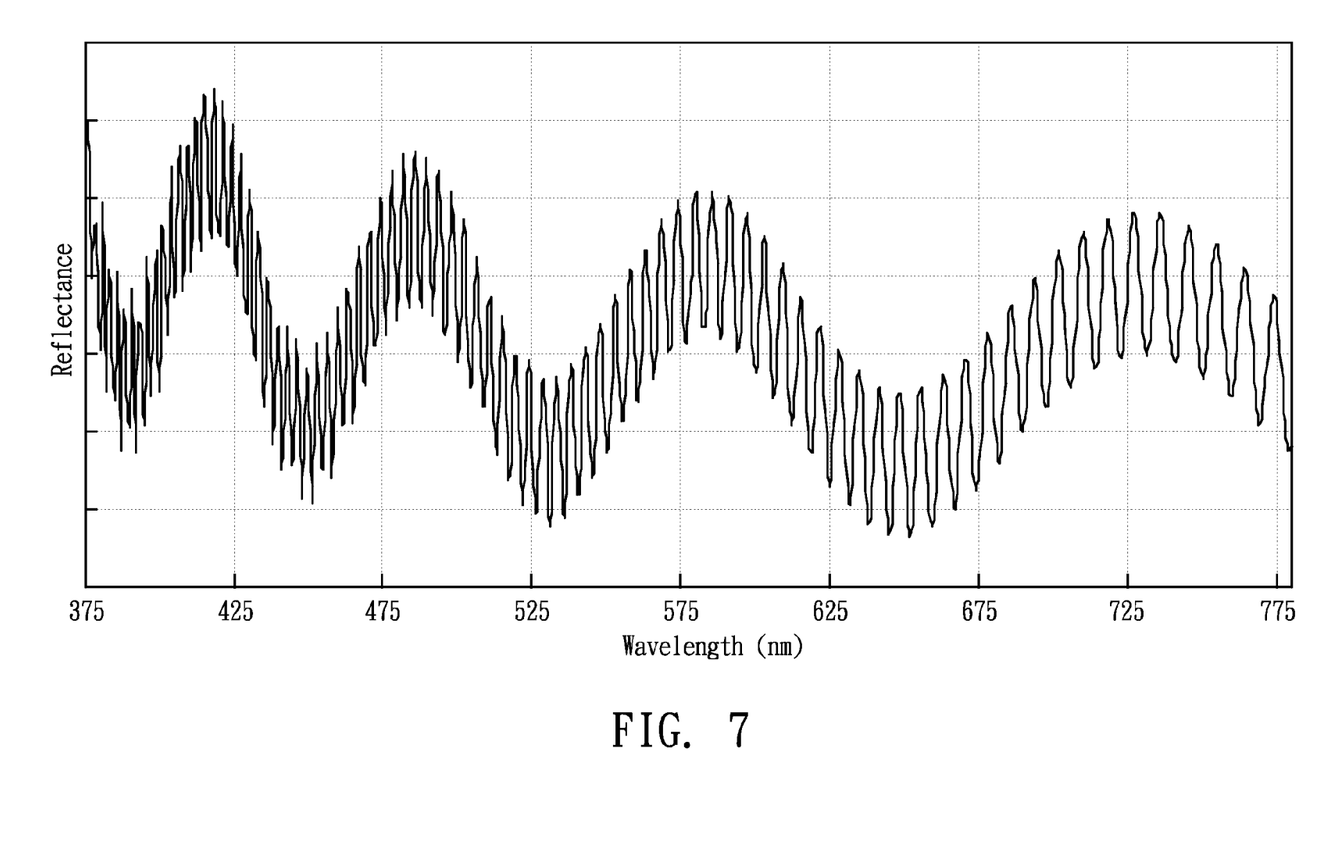
FIG. 7 shows a graphical of the measured diffraction spectrum of a via structure in accordance with an exemplary embodiment.
Figure 8:
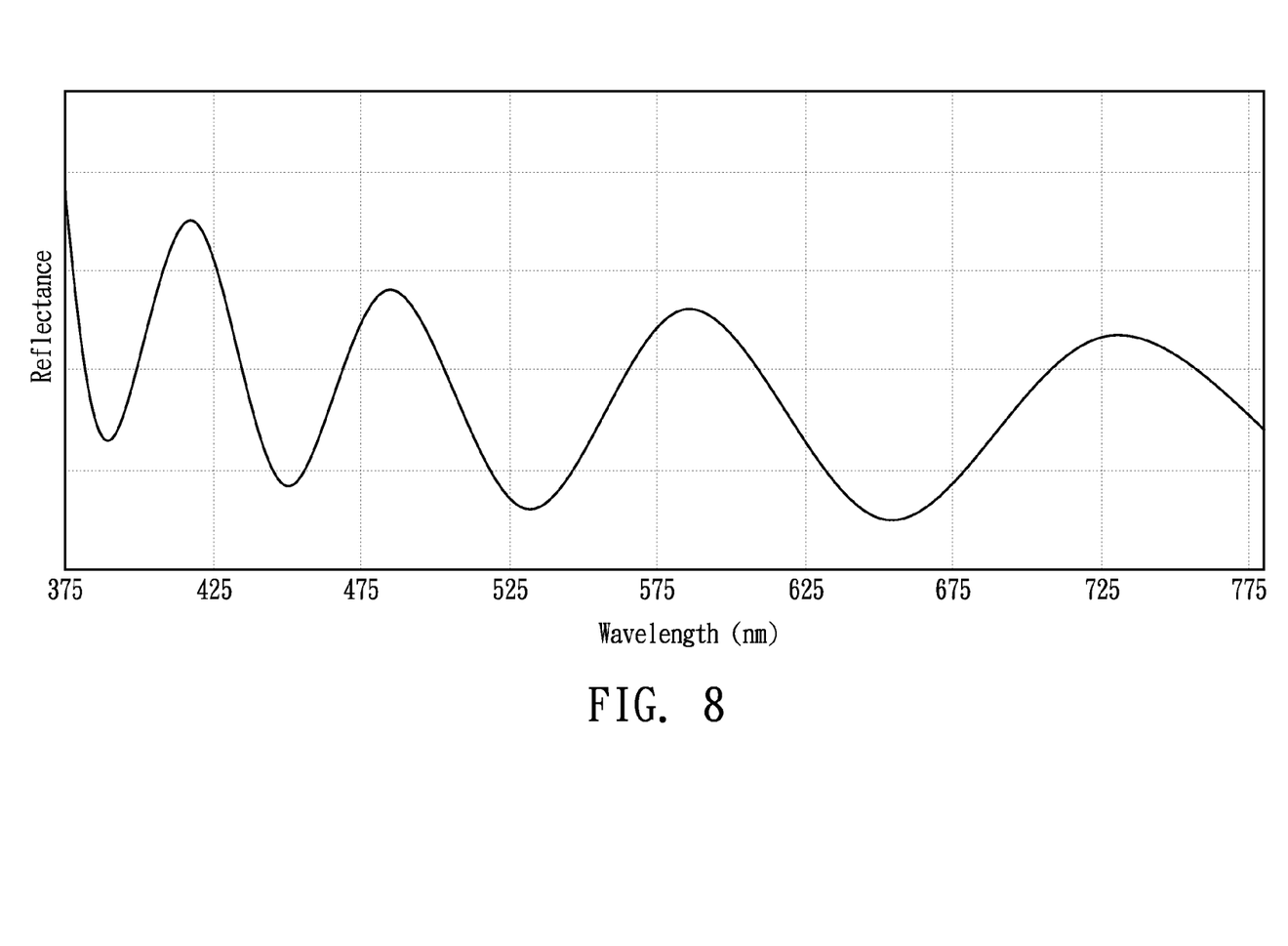
FIG. 8 shows a graphical view of the low-frequency portion of a measured diffraction spectrum in accordance with an exemplary embodiment.
Figure 9:
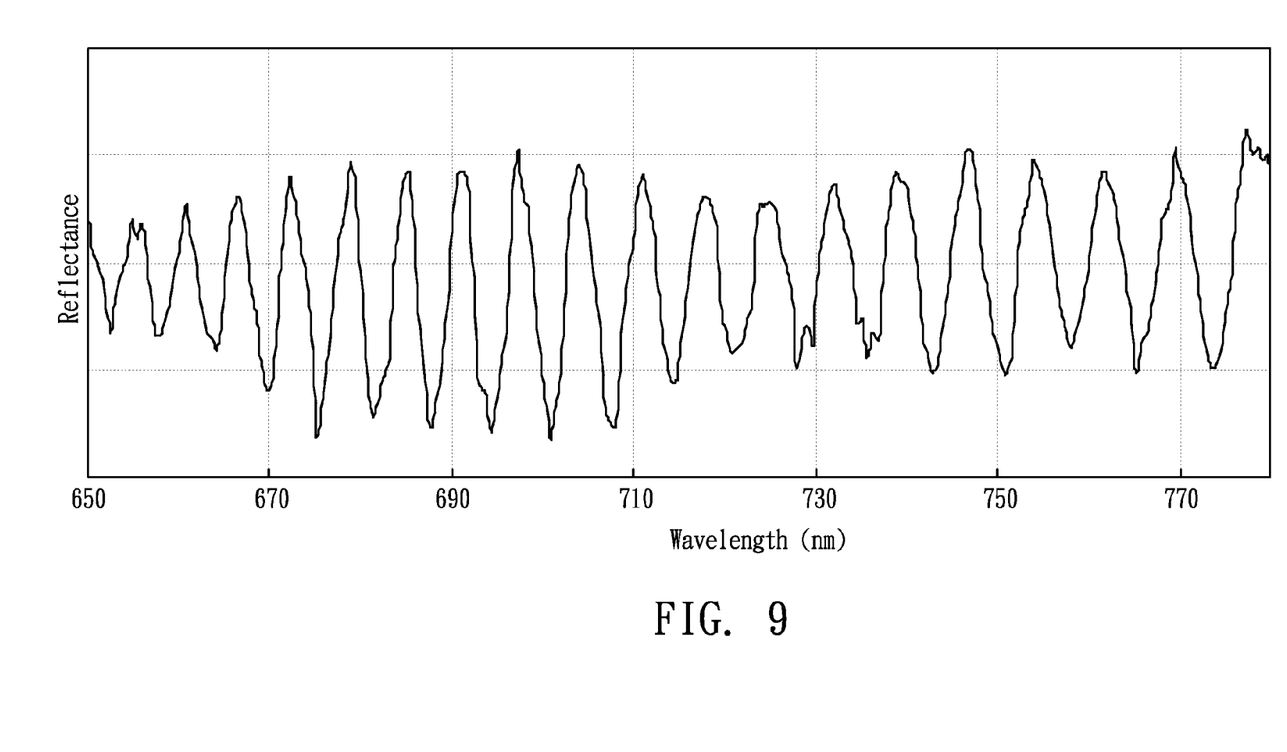
FIG. 9 shows a graphical view of the high-frequency portion of a measured diffraction spectrum in accordance with an exemplary embodiment.

FIG. 7 shows the measured diffraction spectrum of the via structure 600. As shown in FIG. 7, the measured diffraction spectrum comprises a high-frequency portion and a low-frequency portion. The low-frequency portion serves as the carrier frequency of the high-frequency portion. The low-frequency portion corresponds to the thickness of the thin film oxide layer 602. The high-frequency portion corresponds to the depth of the via structure 600. The high-frequency portion and the low-frequency portion shown in FIG. 6 can be separated. FIG. 8 shows the low-frequency portion of the measured diffraction spectrum shown in FIG. 7. FIG. 9 shows the high-frequency portion of the measured diffraction spectrum shown in FIG. 7. Accordingly, the simulation unit 120 simulates different diffraction spectrums for via structures with different depths and thin film oxide layers with different thickness. The comparing unit 130 then selects a simulated diffraction spectrum with a minimum difference compared with the measured diffraction spectrum and determines the thickness of the thin film 602 oxide layer and the depth of the via structure 600.

Figure 10:
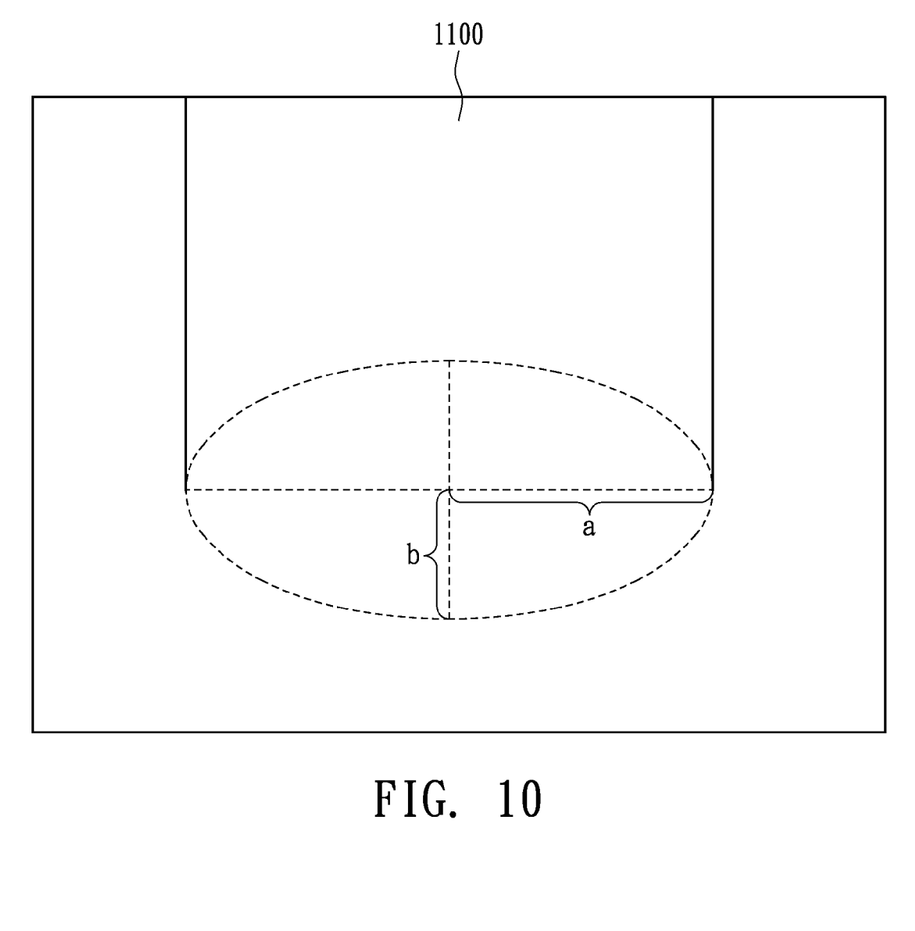
FIG. 10 shows a schematic view of the bottom profile of a via structure.
Figure 11:
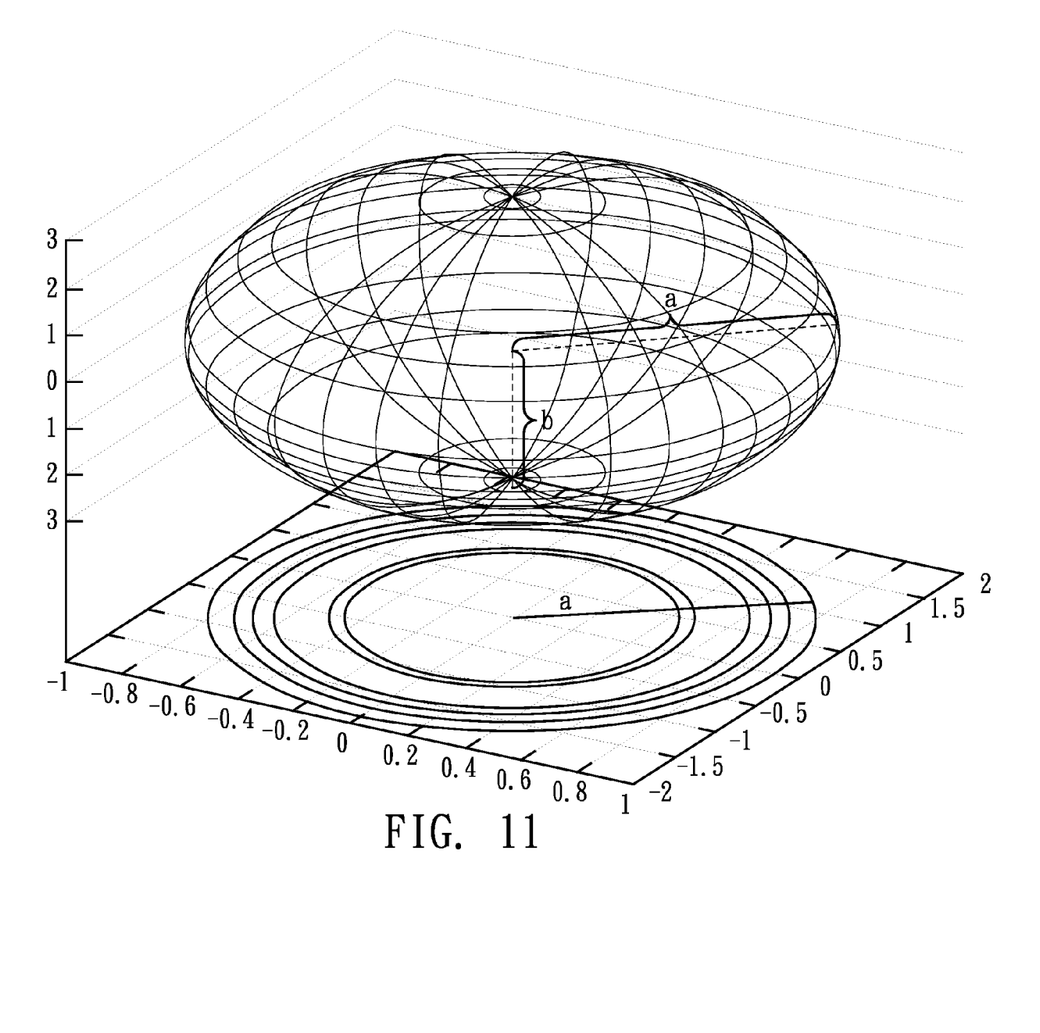
FIG. 11 shows a graphical view of the three-dimensional drawing of an ellipsoid model in accordance with an exemplary embodiment.

An exemplary embodiment of the method for determining via structure parameters according to the reflection spectrums of the via structure uses an ellipsoid model to simulate the bottom profile of the via structure, and determines the bottom profile of the via structure by comparing the collected diffraction spectrum and the simulated diffraction spectrums. FIG. 10 shows the bottom profile of a via structure. As shown in FIG. 10, the longitudinal section of the bottom profile 1100 of the via structure is an ellipse curve. Accordingly, an exemplary embodiment of the method for determining via structure parameters according to the reflection spectrums of the via structure uses an ellipse curve to simulate the bottom profile of the longitudinal section of the via structure, wherein the ellipse curve can be represented by the following equation:

$$\frac{x^2}{a^2} + \frac{y^2}{b^2} = 1$$

where a is the semimajor axis of the ellipse and is the radius of the via structure, and b is the semiminor axis of the ellipse. FIG. 11 shows a three-dimensional drawing of the ellipsoid model. As can be seen from FIG. 11, when b is 0, the ellipsoid model corresponds to a via structure with a flat bottom profile, and when b equals a, the ellipsoid model corresponds to a via structure with bottom profile of round curve.

Figure 12:
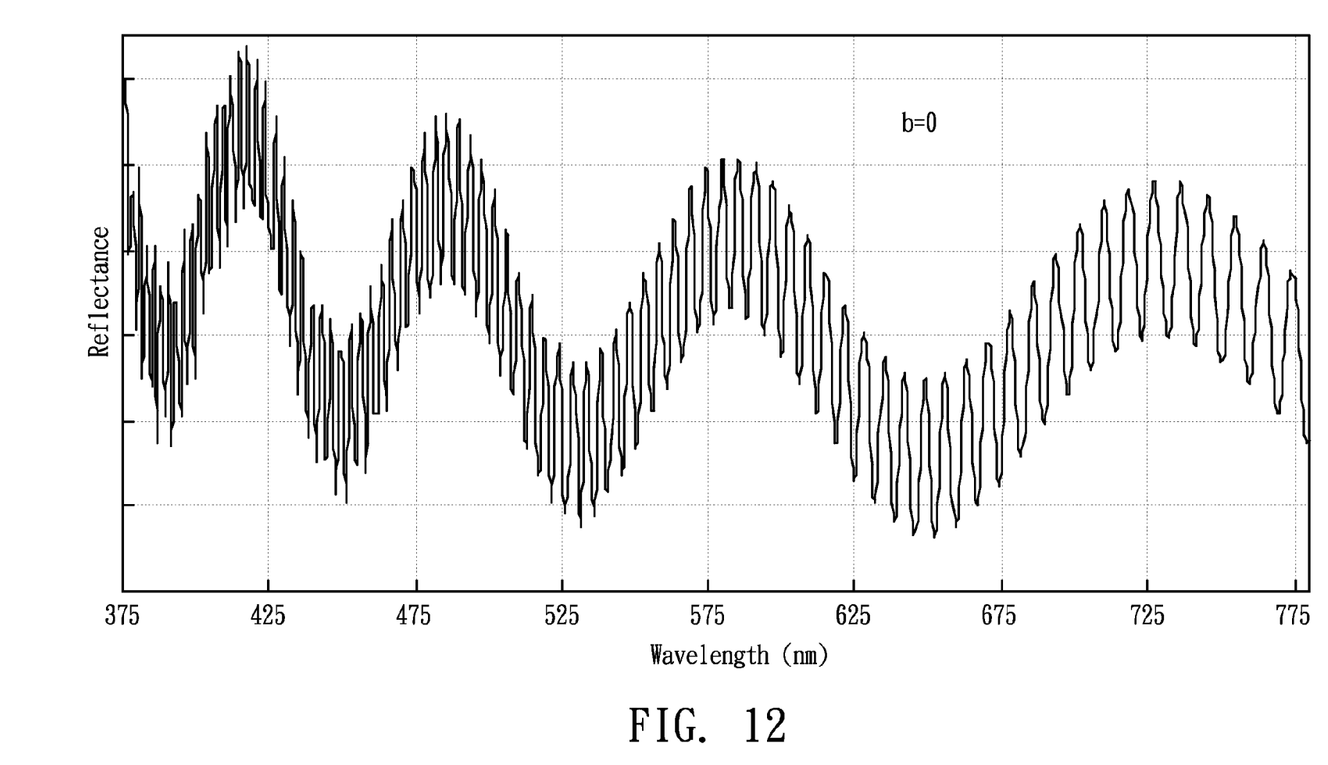
FIG. 12 shows a a graphical view of the diffraction spectrum in accordance with an exemplary embodiment.

Applying the system 100 shown in FIG. 1 and the method shown in FIG. 2 to the bottom profile 1100, if the via structure has a flat bottom profile, the reflectometer 110 collects more reflecting lights. If the via structure has a round bottom profile, the reflectometer 110 collects fewer reflecting lights. Accordingly, if the via structure has a flat bottom profile, the magnitude of the high-frequency portion of the diffraction spectrum thereof is greater, and thus the diffraction spectrum is steeper. If the via structure has a round bottom profile, the magnitude of the high-frequency portion of the diffraction spectrum thereof is smaller, and thus the diffraction spectrum is smoother. FIG. 12 shows the diffraction spectrum of a via structure with a flat bottom profile, i.e. b equals 0.

Figure 13:
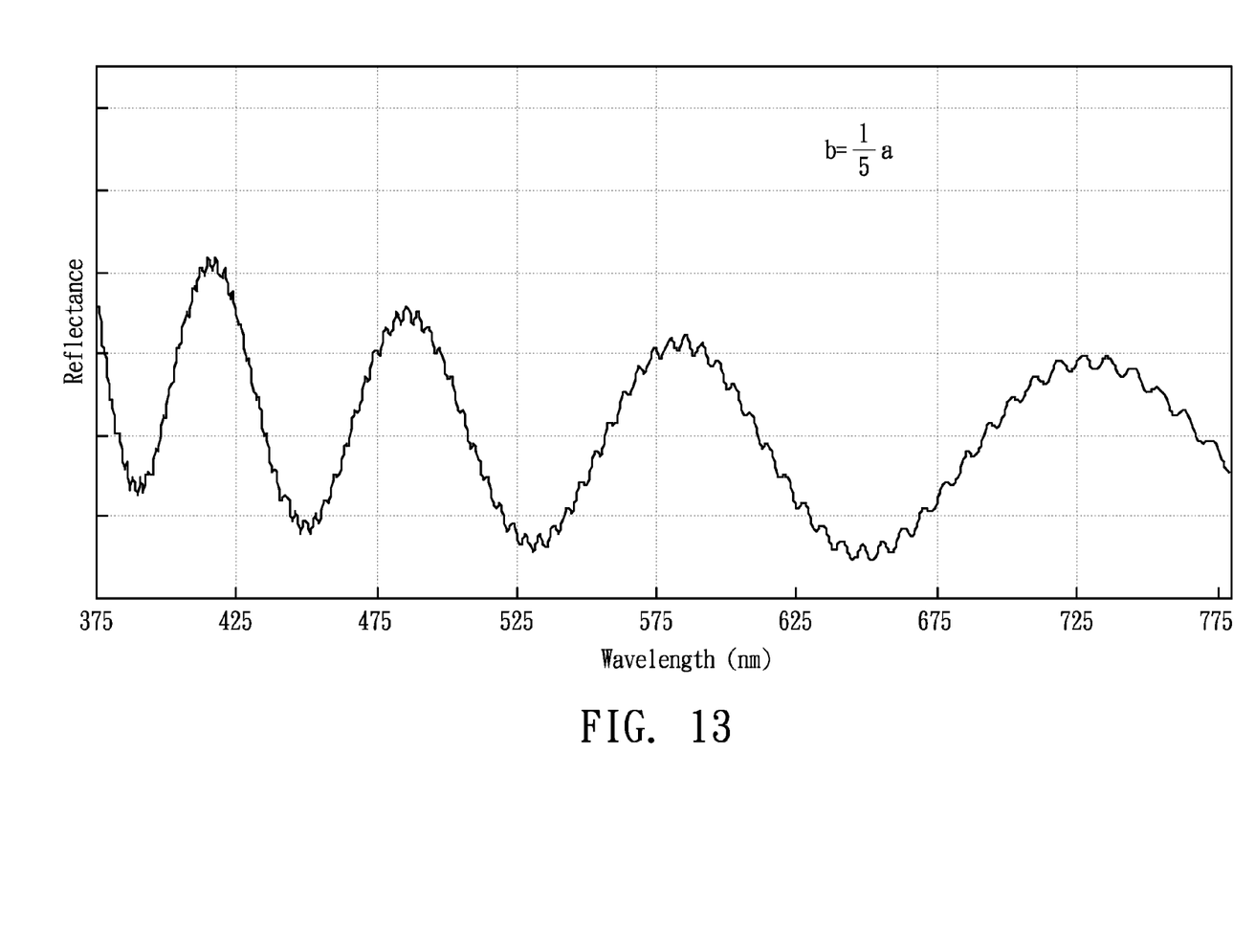
FIG. 13 shows a a graphical view of the diffraction spectrum in accordance with another exemplary embodiment.
Figure 14:
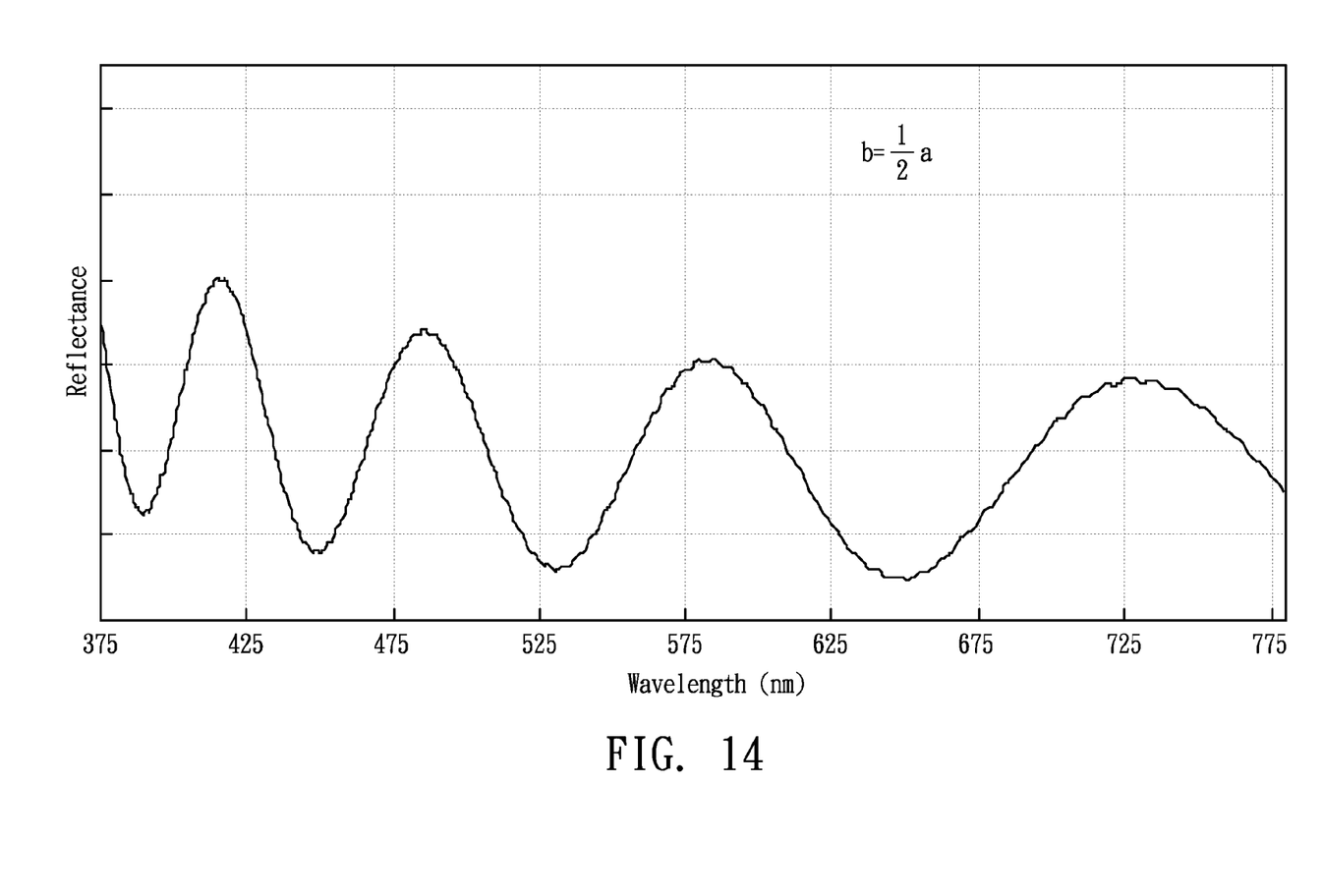
FIG. 14 shows a a graphical view of diffraction spectrum in accordance with yet another exemplary embodiment.

FIG. 13 shows the diffraction spectrum of a via structure in which b equals 0.2 a. FIG. 14 shows the diffraction spectrum of a via structure in which b equals 0.5 a. As shown in FIGS. 12 to 14, the smoothness of the diffraction spectrum of a via structure varies with the flatness of the bottom profile of the via structure.

When utilizing the simulation unit 120 to simulate the bottom profile of a via structure based on an ellipsoid model, the semimajor axis a is a known parameter, which can be obtained according to measurement or manufacture parameters. By varying the semiminor axis b of the ellipsoid model, different diffraction spectrums can be generated. The comparing unit 130 then selects a simulated diffraction spectrum with a minimum difference compared with the measured diffraction spectrum and determines the bottom profile of the via structure according to the parameters, i.e. the semiminor axis b, of the selected simulated diffraction spectrum. Accordingly, the comparing unit 130 can determine the thickness of the thin film oxide layer, the depth of the via structure, and the bottom profile of the via structure according to the comparing results.

The aforementioned exemplary embodiment determines the thickness of the thin film oxide layer, and the depth and bottom profile of a single via structure. However, by analyzing the diffraction spectrums, a plurality of via structures can be determined simultaneously. Further, by changing the parameters of the Fresnel equation of the simulation, the via structures filled with different materials can also be measured.

In conclusion, the exemplary embodiments of the system and method for determining via structure parameters provided by this disclosure can measure the depth and the bottom profile of a via structure in a fast and non-destructive way, and therefore are more suitable for via structure measurement. The above-described exemplary embodiments are intended to be illustrative only. Those skilled in the art may devise numerous alternative embodiments without departing from the scope of the following claims.

We claim:

1. A method for determining via structure parameters according to a diffraction spectrum of at least a via structure, comprising the steps of:
obtaining a measured diffraction spectrum of at least a via structure;
carrying out a calculation based upon frequency information contained in the measured diffraction spectrum; and
determining at least a depth of the at least a via structure according to the calculation results.

2. The method of claim 1, wherein the measured diffraction spectrum comprises a high-frequency portion and a low-frequency portion, the low-frequency portion serves as the carrier frequency of the high-frequency portion, the calculation is based upon the high-frequency portion, and the at least a depth of the at least a via structure is determined according to the calculation results based upon the high-frequency portion.

3. The method of claim 2, wherein the calculation is also based upon the low-frequency portion, and a thickness of an oxide layer on the surface of each of the at least a via structure is determined according to the calculation results based upon the low-frequency portion.

4. The method of claim 1, wherein the calculation is carried out by comparing the measured diffraction spectrum with a plurality of simulated diffraction spectrums corresponding to the at least a via structure obtained according to Fresnel equation, the determination step is applied to select a simulated diffraction spectrum with a minimum difference compared with the measured diffraction spectrum, and then to determine the at least a depth of the at least a via structure according to the parameters of the selected simulated diffraction spectrum.

5. The method of claim 1, wherein the calculation is carried out by performing a Fourier transform of the measured diffraction spectrum, and the at least a depth of the at least a via structure is determined according to the calculation results of the Fourier transform.

6. The method of claim 1, wherein the measured diffraction spectrum is obtained by operating a reflectometer on the at least a via structure.

7. The method of claim 6, wherein the measured diffraction spectrum is obtained by operating a reflectometer on a plurality of via structures simultaneously, and the depths of the via structures are determined simultaneously.

8. A method for determining the bottom profile of at least a via structure according to the reflection spectrums of the at least a via structure, comprising the steps of:
obtaining a measured diffraction spectrum of the at least a via structure;
carrying out a calculation based upon magnitude information contained in the measured diffraction spectrum; and
determining at least a bottom profile of the at least a via structure according to the calculation results.

9. The method of claim 8, wherein the measured diffraction spectrum comprises a high-frequency portion and a low-frequency portion, the low-frequency portion serves as the carrier frequency of the high-frequency portion, the calculation is based upon the magnitude of the high-frequency portion relative to the low-frequency portion, and the at least a bottom profile of the at least a via structure is determined according to the calculation results based upon the magnitude of the high-frequency portion relative to the low-frequency portion.

10. The method of claim 8, wherein the calculation is carried out by comparing the measured diffraction spectrum with a plurality of simulated diffraction spectrums corresponding to the at least a bottom profile of the at least a via structure obtained according to Fresnel equation and an ellipsoid model, the determination step is performed to select a simulated diffraction spectrum with a minimum difference compared with the measured diffraction spectrum, and then the at least a bottom profile of the at least a via structure is determined according to the parameters of the selected simulated diffraction spectrum.

11. The method of claim 10, wherein the longitudinal section of the ellipsoid model is an ellipse, which can be represented by the following equation:

$$\frac{x^2}{a^2} + \frac{y^2}{b^2} = 1$$

where a, which is a known parameter, is the semimajor axis of the ellipse and is the radius of the at least a via structure, b is the semiminor axis of the ellipse, and the determination step is performed to determine the parameter b and thus determine the at least a bottom profile of the at least a via structure.

12. The method of claim 10, wherein the radius of the at least a via structure is obtained according to measurement or manufacture parameters.

13. The method of claim 8, wherein the measured diffraction spectrum is obtained by operating a reflectometer on the at least a via structure.

14. The method of claim 13, wherein the measured diffraction spectrum is obtained by operating a reflectometer on a plurality of via structures simultaneously, and the bottom profiles of the via structures are determined simultaneously.

15. A system for via structure measurement, comprising:
a reflectometer, configured to collect a measured diffraction spectrum of at least a via structure;
a simulation unit, configured to provide simulated diffraction spectrums of the at least a via structure; and
a comparing unit, configured to determine at least a depth and at least a bottom profile of the at least a via structure by comparing the collected measured diffraction spectrum of at least a via structure and the simulated diffraction spectrums of the at least a via structure.

16. The system of claim 15, wherein the simulation unit is a database, which stores a plurality of simulated diffraction spectrums of via structures with different depths and different bottom profiles.

17. The system of claim 15, wherein the simulation unit is a computer, which is configured to generate simulated diffraction spectrums of via structures with different depths and different bottom profiles.

18. The system of claim 15, wherein the simulated diffraction spectrums of the at least a via structure are generated based upon Fresnel equation.

19. The system of claim 15, wherein the simulated diffraction spectrums of the at least a via structure are generated according to an ellipsoid model, which simulates the at least a bottom profile of the at least a via structure.

20. The system of claim 19, wherein the longitudinal section of the ellipsoid model is an ellipse, which can be represented by the following equation:

$$\frac{x^2}{a^2} + \frac{y^2}{b^2} = 1$$

where a, which is a known parameter, is the semimajor axis of the ellipse and is the radius of the at least a via structure, b is the semiminor axis of the ellipse, and the comparing unit is configured to determine the parameter b and thus determine the at least a bottom profile of the at least a via structure.

21. The system of claim 20, wherein the radius of the at least a via structure is obtained according to measurement or manufacture parameters.

* * * * *